United States Patent [19]

Saupe

[11] Patent Number: 5,542,433
[45] Date of Patent: Aug. 6, 1996

[54] LEG TO WAIST PRISONER RESTRAINT

[76] Inventor: Brian Saupe, P.O. Box 473341, Aurora, Colo. 80017

[21] Appl. No.: 328,854

[22] Filed: Oct. 25, 1994

[51] Int. Cl.[6] .............................. A61F 5/37; E05B 75/00
[52] U.S. Cl. ................. 128/869; 128/876; 70/16
[58] Field of Search .................... 128/845, 846, 128/869–879; 602/5, 12; 70/14–16

[56] References Cited

U.S. PATENT DOCUMENTS

| | | | |
|---|---|---|---|
| 2,295,806 | 9/1942 | Peterson | 128/878 |
| 3,502,073 | 3/1970 | Stanley | 128/876 |
| 4,004,583 | 1/1977 | Johnson | 128/876 |
| 4,426,079 | 3/1982 | Mason | 273/84 R |
| 4,620,535 | 11/1986 | Nesbitt | 128/876 |
| 4,660,552 | 4/1987 | Latham | 128/878 |
| 4,995,672 | 6/1990 | Corcoran | 297/483 |
| 5,159,728 | 1/1991 | Bingold | 24/16 PB |
| 5,172,703 | 12/1992 | Tiede | 128/869 |
| 5,190,055 | 3/1993 | O'Connor | 128/869 |

Primary Examiner—Michael A. Brown

[57] ABSTRACT

A soft restraint to restrain a prisoner's legs together and in a position behind the prisoner's buttocks to prevent the prisoner from kicking and resisting. The restraint is light weight, flexible, and compact enough to carry in a pants or jacket pocket. The restraint consists of an adjustable waist belt secured around the prisoner's waist with a quick release buckle. The waist belt is attached to an ankle belt which is to be placed around the prisoner's ankles and tightened by pulling the belt through a one way buckle. The feet are then pulled up to the rear of the waist belt by pulling the leg to waist strap through an upper one way buckle. The end of the leg to waist strap is then attached back to the ankle belt by clipping it to a metal ring on the ankle belt. This prevents injuries to the prisoner's wrists due to not having the feet connected to the handcuffs worn by the prisoner. The restraint fits all sizes of waists and ankles.

1 Claim, 1 Drawing Sheet

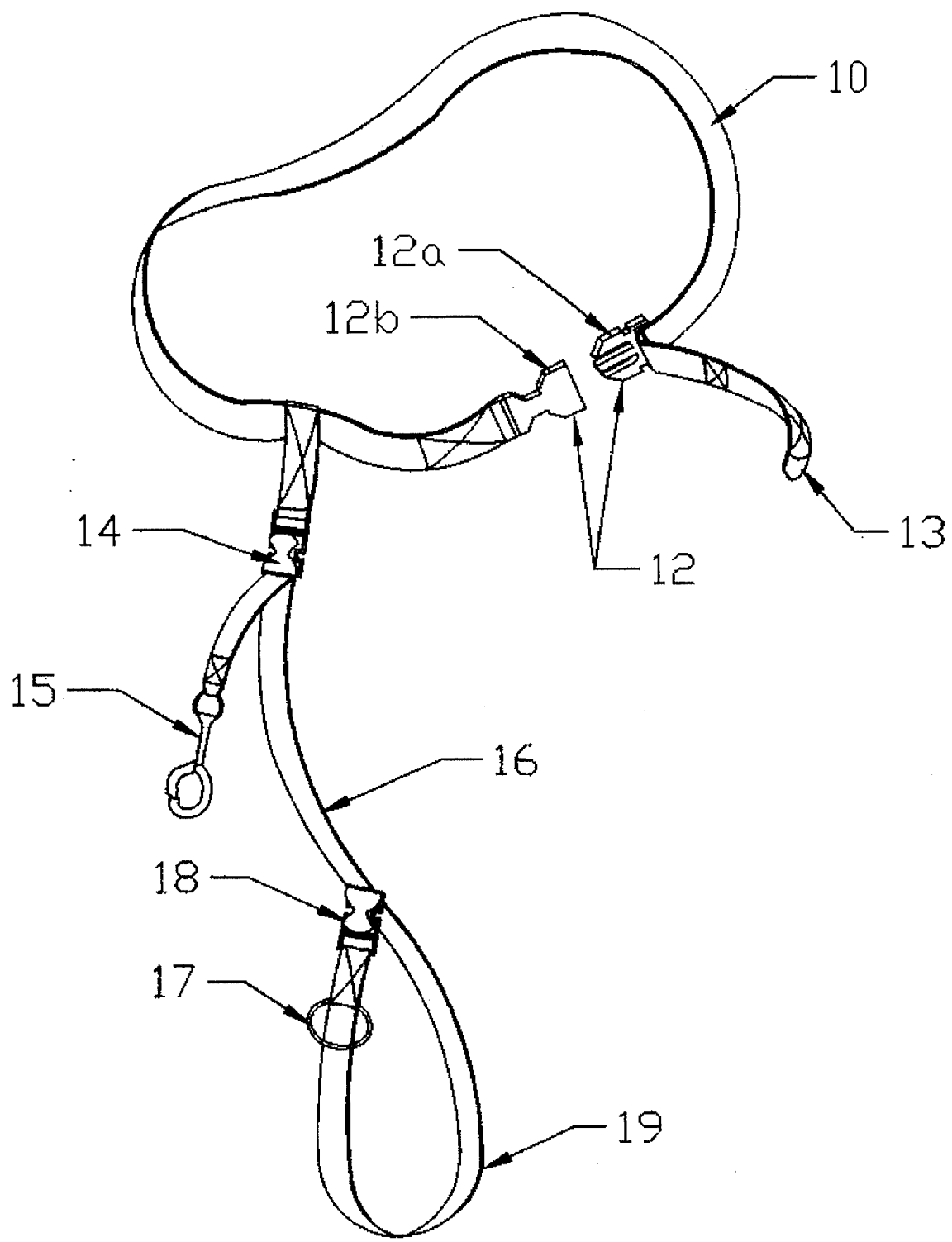

LEG TO WAIST PRISONER RESTRAINT

BACKGROUND

1. Field of the Invention

This invention is a device to be used by law enforcement officers to restrain combative prisoners.

2. Description of Prior Art

In the past, combative prisoners were restrained with their hands handcuffed behind their back. Their legs were then tied together with a rope or strap which had a clip at each end. One clip would be placed on the rope to form a loop which was placed around the prisoner's ankles, then pulled tight. The feet were then pulled up behind the prisoner's buttocks and the clip on the loose end of the rope was attached to the handcuff chain, between the prisoner's hands. The ropes used commonly became tangled and twisted. They also did not hold the prisoner's feet together on their own. The most serious problem caused with this method was that it caused serious nerve damage injuries in the prisoner's wrists. These injuries have only developed recently, resulting in several law suits against police officers and their departments. This has prompted several police departments to forbid their officers to use the above method of prisoner restraint. This has left officers with no effective alternative. A patent search revealed that the above mentioned devices were not patented.

OBJECTS AND ADVANTAGES

Accordingly, several objects and advantages of the leg to waist prisoner restraint are:

(a) to avoid the above mentioned wrist injuries to prisoners by attaching the restrained feet to a waist belt rather than the handcuff chain.

(b) to provide a restraint that is light weight, flexible, and compact enough to be carried in a pants or jacket pocket without becoming tangled.

(c) to provide a restraint that will not loosen on its own after it is applied, allowing the prisoner to free his feet and kick.

(d) to provide a restraint that is strong enough and adjustable enough to be used on people of various sizes and strengths.

Further objects and advantages of the leg to waist prisoner restraint will become apparent from a consideration of the drawings and ensuing description.

DRAWING FIGURES

FIG. 1 is a full view of the leg to waist prisoner restraint.

| 10 | waist belt | 15 | bolt clip |
|----|------------|----|-----------|
| 12 | quick release buckle | 16 | leg to waist strap |
| 12a | male buckle | 17 | bolt clip ring |
| 12b | female buckle | 18 | lower one way buckle |
| 13 | handloop | 19 | ankle belt |
| 14 | upper one way buckle | | |

DESCRIPTION—FIG. 1

FIG. 1 shows a full view of a basic version of the leg to waist prisoner restraint. A waist belt 10 is a narrow belt with a quick release buckle 12 to connect the two ends around the waist of a prisoner. A male buckle 12a allows the waist belt 10 to be adjusted by pulling on the hand loop 13, making the waist belt 10 smaller. The rear center of the waist belt 10 is connected to an upper one way buckle 14 to secure a leg to waist strap 16 to an ankle belt 19. The leg to waist strap 16 runs through an upper one way buckle 14 to pull the ankle belt 19 up to the waist belt 10. This is done by pulling a bolt clip 15 which is then clipped onto a bolt clip ring 17 attached to the ankle belt 19.

The ankle belt 19 is a narrow belt with a lower one way buckle 18 at one end which forms a loop of the ankle belt 19. The ankle belt 19 is placed around the prisoner's ankles. It is then tightened to secure the ankles together by pulling the leg to waist strap 16.

OPERATION—FIG. 1

The operation of the leg to waist prisoner restrain begins by physically holding the handcuffed prisoner's legs together, on the ground, face down. The ankle belt 19 is placed around both of the prisoner's ankles with the lower one way buckle 18 behind the prisoner's calves.

The leg to waist strap 16 is then pulled upward, causing the lower one way buckle 18 to slide down the ankle belt 19, tightening the ankle belt 19 around the prisoner's ankles. The lower one way buckle 18 prevents the ankle belt 19 from becoming loose around the prisoner's ankles. The ankle belt 19 is tightened enough to prevent the prisoner from moving his ankles apart or pulling his feet free.

The quick release buckle 12 is then disengaged. The hand loop 13 and the male buckle 12a are then placed over the handcuffed hands of the prisoner, under the prisoner's left arm, and then around the prisoner's waist, clockwise. The quick release buckle 12 is then engaged on the prisoner's right side by inserting the male buckle 12a into the female buckle 12b. The waist belt 10 is then tightened, until snug around the prisoner's waist, by pulling the hand loop 13 away from the prisoner's body.

The prisoner's feet are then pulled up to a position behind his buttocks by pulling the bolt clip 15 towards the prisoner's feet from the upper one way buckle 14. The upper one way buckle 14 hold the prisoner's feet securely in this position.

The excess leg to waist strap 16 is then wrapped around the prisoner's ankle to take up any slack that there may be. The bolt clip 15 at the end of the leg to waist strap 16 is then clipped to the bolt clip ring 17 which is attached to the ankle belt.

SUMMARY, RAMIFICATIONS, AND SCOPE

Accordingly, the reader will see that the leg to waist prisoner restraint provides a convenient, effective, and easy to use method of restraining combative prisoners. It also prevents the serious injuries to prisoners' wrists while protecting the safety of the police officers restraining the prisoner.

While the above description contains many specifications, these should not be construed as limitations on the scope of the restraint, but rather as an exemplification of one preferred embodiment thereof. Many other variations are possible. For example, if the prisoner's legs only need to be restrained by tying them together, only the ankle belt portion of the restraint could be used. If the prisoner's legs need to be secured while he is seated in a car, the waist belt portion of the restraint can be placed outside the car door with the door closed to prevent him from raising his legs into a kicking position. The construction of the restraint may be accomplished using several different materials. For example, the width of the waist belt, ankle belt, and leg to waist strap can be varied in order to fit different sized prisoners. There are also several different types of buckles and clips that could be used in place of the quick release buckle, upper one way buckle, lower one way buckle and bolt clip.

I claim:

1. A portable soft restraint device for immobilizing a combative prisoner in the field by securing the prisoner's legs to the prisoner's waist, behind the prisoner's back, said restraint comprising an integrated set of at least two straps, said straps comprising:

(a) an ankle belt of flexible material having a sufficient length to surround both ankles of the prisoner, said ankle belt having a one-way buckle secured thereto to allow said ankle belt to be adjusted in one direction;

(b) a waist belt of flexible material having sufficient length to surround the waist of the prisoner, said waist belt having two ends which can be secured together with a quick, release adjustable buckle;

(c) a leg strap;

said ankle belt is attached to said waist belt by said leg strap and a one-way adjustable buckle which is attached to the side of said waist belt.

* * * * *